United States Patent
Gomez

(10) Patent No.: US 8,152,717 B2
(45) Date of Patent: Apr. 10, 2012

(54) DEVICE FOR WHITE BALANCING AND APPYING AN ANTI-FOG AGENT TO MEDICAL VIDEOSCOPES PRIOR TO MEDICAL PROCEDURES

(76) Inventor: Ricardo Alexander Gomez, Rego Park, NY (US)

( * ) Notice: Subject to any disclaimer, the term of this patent is extended or adjusted under 35 U.S.C. 154(b) by 1243 days.

(21) Appl. No.: 11/908,447

(22) PCT Filed: Jan. 29, 2007

(86) PCT No.: PCT/US2007/002428
§ 371 (c)(1),
(2), (4) Date: Sep. 12, 2007

(87) PCT Pub. No.: WO2007/089719
PCT Pub. Date: Aug. 9, 2007

(65) Prior Publication Data
US 2008/0161646 A1 Jul. 3, 2008

Related U.S. Application Data

(60) Provisional application No. 60/763,472, filed on Jan. 30, 2006.

(51) Int. Cl.
*A61B 1/06* (2006.01)
*H04N 9/73* (2006.01)
(52) U.S. Cl. ............... 600/169; 600/160; 348/223.1
(58) Field of Classification Search .......... 600/129, 600/157–159, 169, 175, 154; 348/223.1–225.1
See application file for complete search history.

(56) References Cited

U.S. PATENT DOCUMENTS

| | | | |
|---|---|---|---|
| 4,831,437 A * | 5/1989 | Nishioka et al. | 348/71 |
| 5,111,804 A | 5/1992 | Funakoshi | |
| 5,852,494 A | 12/1998 | Skladnev et al. | |
| 5,880,779 A * | 3/1999 | Rhynes | 348/223.1 |
| 6,117,070 A * | 9/2000 | Akiba | 600/154 |
| 2002/0022762 A1 | 2/2002 | Beane et al. | |
| 2005/0234301 A1 | 10/2005 | Gomez | |

FOREIGN PATENT DOCUMENTS

JP 64005525 * 1/1989
WO WO2005096916 A1 * 10/2005

OTHER PUBLICATIONS

International Search Report dated Oct. 25, 2007.

* cited by examiner

*Primary Examiner* — Matthew J Kasztejna
*Assistant Examiner* — Ryan Henderson
(74) *Attorney, Agent, or Firm* — McCormick, Paulding & Huber LLP

(57) ABSTRACT

A device is configured for white balancing a medical videoscopic camera system prior to videoscopic medical procedures, as well as optionally simultaneously or non-simultaneously applying a fog-prohibiting agent to the distal lens of a medical videoscope such as an endoscope or laparoscope. The device combines a white balancing mechanism, protective mechanism, and defogging mechanism in one simple easy to use device.

30 Claims, 9 Drawing Sheets

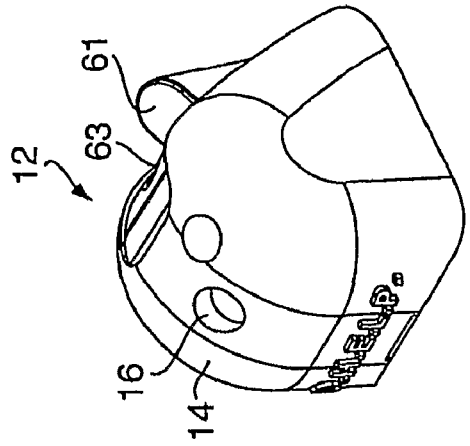
FIG. 3A
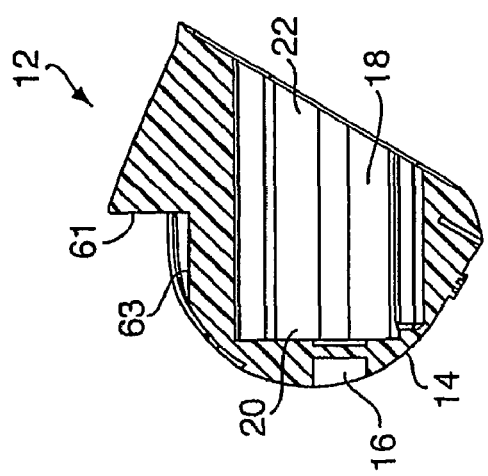
FIG. 3F
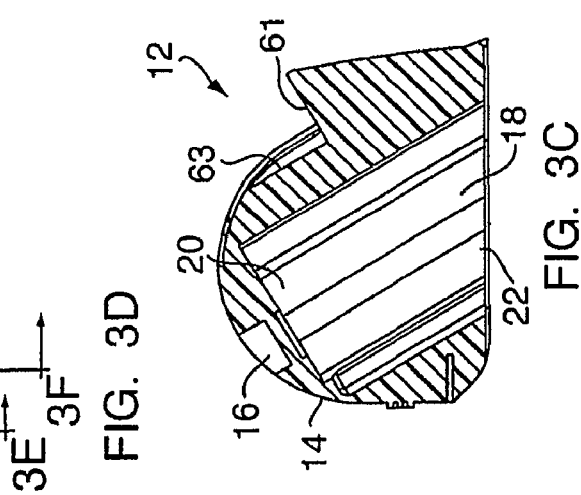
FIG. 3D
FIG. 3C
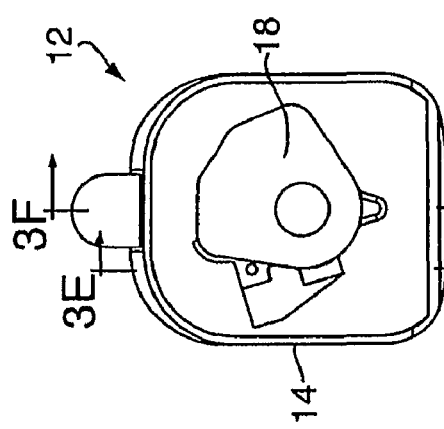
FIG. 3E
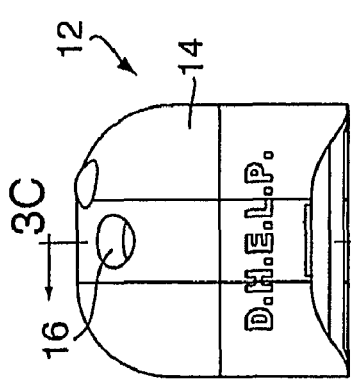
FIG. 3B

DEVICE FOR WHITE BALANCING AND APPYING AN ANTI-FOG AGENT TO MEDICAL VIDEOSCOPES PRIOR TO MEDICAL PROCEDURES

CROSS-REFERENCE TO RELATED APPLICATION

This application claims the benefit of U.S. Provisional Application No. 60/763,472, filed on Jan. 30, 2006, the disclosure of which is hereby incorporated by reference in its entirety.

FIELD OF INVENTION

This invention generally relates to a device for white balancing a camera, and more specifically relates to a device for white balancing a medical videoscopic camera system prior to videoscopic medical procedures, as well as optionally simultaneously or non-simultaneously applying a fog-prohibiting agent to the distal lens of a medical videoscope such as, for example, an endoscope, laparoscope, bronchoscope, cystoscope or otoscope. The device combines a white balancing mechanism, protective mechanism, and defogging mechanism in one simple easy to use device.

BACKGROUND

The color of light reflected off of a subject changes with the color of the light source. Unlike a human eye, a digital camera is unable to adapt to these changes. The human eye/brain automatically compensates for the color temperature of light falling on an object. When you move from the bright, blue-tinted sunlight to the dim, yellow-tinted indoor lighting, your eye automatically adjusts to the different color of light and changes your perception accordingly. If your brain knows it is looking at something white, it will look white in bright sunlight or inside even under a fluorescent light. Unfortunately, even the most expensive video cameras cannot automatically do what the eye does, so we have to show our cameras what we want them to read as "white" in any given scene.

In most digital cameras, the illumination intensity and color temperature must be measured and adjusted to ensure that a white object is recorded as white. This process is often referred to as white balancing, and is a software or hardware option on all digital cameras. It is important with digital cameras to white balance manually for the absolute best video output results.

White balancing is an important function that is carried out with all digital endoscopic and laparoscopic cameras prior to videoscopic medical procedures. Normally our eyes compensate for lighting conditions with different color temperatures. A digital camera needs to find a reference point which represents white. It will then calculate all the other colors based on this white point.

The RGB system is one of the primary color models used to specify and represent colors in computer-controlled cameras and software. White is produced by combining equal parts of all three colors (red, green and blue) at levels of 100 percent. In white balancing a camera, a sensor on or within the camera averages the light within the scene and automatically adjusts the camera's internal color balance to zero-out any generalized color bias. By finding the difference between the white the camera sees and that of the internal reference white, the camera can adjust for the difference for every other color, thereby generating a more accurate and realistic video image. Even professional photographers who use digital still cameras carry a white reference card to properly white balance in order to capture the most accurate life-like images. It is amazing that today, in the advanced medical procedures requiring realistic and accurate video images, white balancing is rarely done correctly.

The video color quality is very much dependant on the accuracy of the white balance performed prior to the medical procedure. This is especially important in laparoscopic and endoscopic cameras that are involved in life and death situations. A realistic video image is crucial when trying to differentiate between slight pigmentation changes in tissues while looking for inflammation, metastasis during cancer resections or diagnostic procedures.

Often, doctors do not understand the importance of white balancing and so they will use a reference such as surgical gauze—which is actually full of holes and not truly white—to set the calibration. Moreover, white balancing is carried out in the open room where there is different light sources illuminating the "white" gauze sponge; this is a problem because the video inside the body will be generated using only the camera's fiber optic light source. Both of these mistakes generate an incorrect white balance point. Consequently, the video images generated often have a color shift away from the real colors. For photography, this is annoying. For medicine this can be dangerous. Moreover, doctors also often hold the scope too close to the white target distorting the camera's light, or too far exposing the white to room fluorescent lights and spot lights.

Laparoscopic and endoscopic cameras are involved in life and death situations, such as trying to differentiate between slight pigmentation changes in tissues when looking for inflammation or metastasis during cancer resections. Another problem is that, currently, white balancing the medical videoscope during medical procedures is a hassle. The surgeon has to coordinate with the nurse for the right time to white balance. The doctor is often sterile and cannot press the white balance button on the camera equipment. He or she must hold the sterile scope facing the "white" gauze and at the same time synchronize with the nurse to press the white balance button in the equipment. This becomes complicated and time consuming because the nurse often is busy when the surgeon is ready to white balance or the surgeon is busy when the nurse is ready to white balance. This wastes time, and time is very expensive in the operating room.

Additionally, from the birth of endoscopic and laparoscopic surgery to the present, surgeons have continually dealt with a persistent and annoying problem, the fogging of the scope lens. The fogging of the scope is very costly. When scopes fog up during surgery, the surgeon cannot see and must pause the surgery until the picture can be cleared up. This routine commonly occurs at least several times during every procedure. With the incredible costs relating to anesthesia and surgical staff, the wasted time in the aggregate equals hundreds and thousands of dollars.

Condensation on the lens occurs because there are temperature differences which occur initially when the cold scope enters the warm moist body, and transiently during the procedure when the doctor coagulates tissue. Since many medical procedures are sterile, current methods to solve both these visualization problems are limited to messy anti-fog solutions and inaccurate white balancing techniques.

Another major problem is that the white reference must often be sterile, so doctors typically use the "white" surgical gauze sponge to white balance. These sponges are in reality full of holes and actually not the ideal white. By white balancing with an off-white, that is illuminated by different lights with different color temperatures, doctors are settling for below optimum video image quality. Ultimately, this may distort the accuracy of the white balance and diminish the quality and the true reproduction of the color in the video generated from inside the body during the medical procedure. Having below optimum video color quality could be dangerous as inflammation and cancer metastasis often presents as discreet color changes. This is becoming more and more important as endoscopes and laparoscopes are becoming vital diagnostic instruments.

SUMMARY OF THE INVENTION

In an aspect of the present invention, a device for white balancing a medical videoscope such as, for example, an endoscope or laparoscope includes a housing having an outer surface defining an opening, an interior of the housing defining a canal having a first end communicating with the opening and a second end terminating within the housing for receiving a distal lens of a medical videoscope, and a white balancing reference material disposed adjacent to the second end of the canal.

It is an object of the present invention to provide a device for a multi-function device which is used for white balancing medical videoscopic cameras as well as an applicator for applying an anti-fog agent such as a liquid, gel or coating to the medical videoscope prior to a medical procedure.

The present invention entails a small, sterile, single patient use, disposable device containing an internal canal with a true white colored target at the end of the canal. The true white color inside the device is formulated to match the RGB combination most commonly used as internal reference true white for medical videoscopic digital camera systems. The target can be a painted surface, fabric pad, or another cushioning material, preferably a foam sponge. The target is designed to allow a space for the light to reflect, preferably with a concave space in the center of the foam sponge. Contained within the canal or in a reservoir surrounding the sponge is an anti-fog agent used to prevent fogging of the scope. This agent is preferably a surfactant wound cleaning solution that both inhibits fog and aids in the cleaning of the scope.

The device is sterile and is opened prior to beginning a medical procedure. After the device is opened on a supply table, the nurse or doctor can place the device over the distal end of the medical videoscope. Inside the device, the distal lens of the scope faces a white material that covers the entire viewing area. The doctor or nurse then presses the white balance button on the camera equipment and the digital camera uses the white sponge as the reference white and properly executes the white balance calibration. The white target is optionally submerged in or impregnated with an anti-fog agent that is simultaneously or non-simultaneously applied to the distal lens upon the insertion of the distal scope into the device. The defogging mechanism can be activated and an antifog agent applied to the scope at the beginning and intermittently during the procedure. The device provides an environment for the scope which facilitates easy and accurate white balancing for medical videoscopes prior to and during medical procedures.

More specifically, the present invention relates to a single patient use, sterile device that contains a tunnel space within it. At the innermost end of the tunnel is contained a white colored light diffusing material. The material can be a colored surface, cushion, fabric pad, or foam sponge. The material is impregnated or submerged in an anti-fog agent such as a liquid, a gel, a coating, or a surfactant cleaning solution which also has antifog properties. The white sponge has a specifically formulated white color to facilitate white balancing. White is generated from the equal combination of different colors. The true white material in the device is the same RGB combination most commonly used as internal reference white for medical videoscopic digital camera systems. The true white material can also be impregnated with a wound cleaning surfactant solution or be used to scrub the distal lens while the scope is inserted in the device.

The device is placed over the distal lens of a medical videoscope such as an endoscope or laparoscope. By placing the scope inside the device and then activating a white balance button on the camera equipment, the scope is white balanced correctly and conveniently. The optimum white balance is achieved by not only using a true white reference but also by illuminating the white reference solely with the camera's light source. During medical procedures, white balancing is currently done in the open room which is illuminated by fluorescent lights and spot lights. This conventional way of white balancing is a mistake, since inside the body the only light illuminating the organs is a fiber optic light.

Additionally, when the scope is inside the device for white balancing, the lens is making simultaneous contact with a solution or agent formulated to inhibit fog on the medical videoscope or aid in cleaning blood and debris from the lens. The liquid additionally provides an improvement in visualization. Fog is a major problem during endoscopic surgery. When cold scopes are introduced into the warm moist body, condensation occurs. This condensation fogs the viewing area forcing the procedure to be delayed until it clears up.

What is needed is a device that not only makes white balancing accurate and easy but also a device which includes a defogging mechanism. The defogging mechanism may be with the use of a cold anti-fog liquid or and electrical or exothermic mechanism that heats the anti-fog liquid. The device is opened prior to any medical procedure and placed over the distal lens of the medical videoscope. White balancing is performed by pressing the white balance button in the camera equipment. The device is then removed from the distal scope immediately prior to its insertion into the body and can be reinserted into the device whenever the scope is removed from the body. The device is sterile, for single patient use, and can be discarded after each procedure or kept on the distal scope until the scope is resterilized.

Additionally even with a perfect white, it is vital that the scope lens be held at a certain minimum distance from the white target for the light to properly reflect. The device provides a mechanism that provides a consistent, set space between the scope lens and the true white target. This space is also part of the defogging mechanism. Within the device a collection of an antifog agent is kept. When the doctor decides, he can activate a mechanism which forces the defogging liquid to rush out of the reservoir and into the space between the white target and the scope. The scope lens is thoroughly covered with the antifog agent.

BRIEF DESCRIPTION OF THE DRAWINGS

These objects and features of the invention will be more clearly understood from the following detailed description along with the accompanying drawing figures, wherein:

FIG. 3A is a front perspective view showing a housing of the device.

FIG. 3B is a front view of the housing of FIG. 3A.

FIG. 3C is a cross-sectional view of the housing taken along the lines 3C-3C of FIG. 3B.

FIG. 3D is a top view of the housing.

FIG. 3E is a cross-sectional view of the housing taken along the lines 3E-3E of FIG. 3D.

FIG. 3F is a cross-sectional view of the housing taken along the lines 3F-3F of FIG. 3D.

DETAILED DESCRIPTION OF THE PREFERRED EMBODIMENTS

Figure 5A:
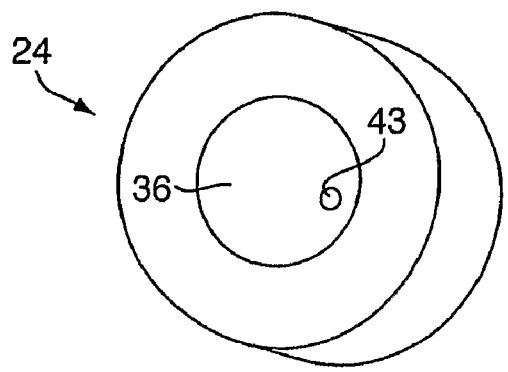
FIG. 5A is a perspective view of a white balancing reference material.
Figure 5B:
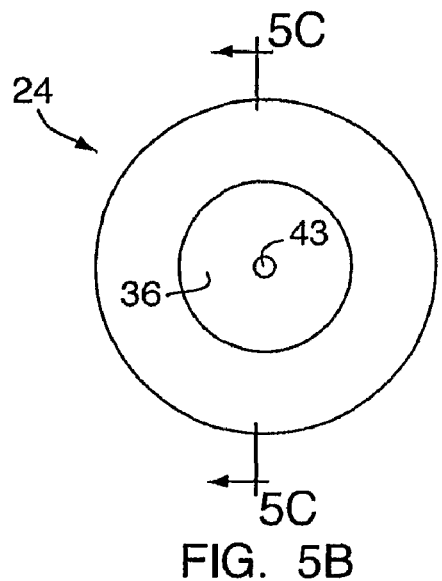
FIG. 5B is a top plan view of the reference material.
Figure 5C:
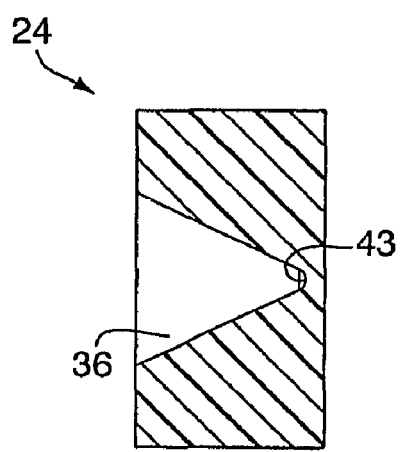
FIG. 5C is a cross-sectional view of the reference material taken along the lines 5C-5C of FIG. 5B.
Figure 6A:
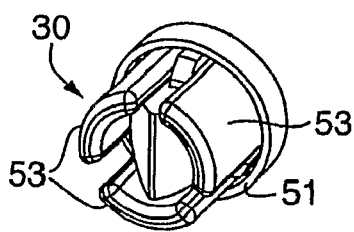
FIG. 6A is a perspective view of an embodiment of a self-sealing mechanism of a white balance device.
Figure 6B:
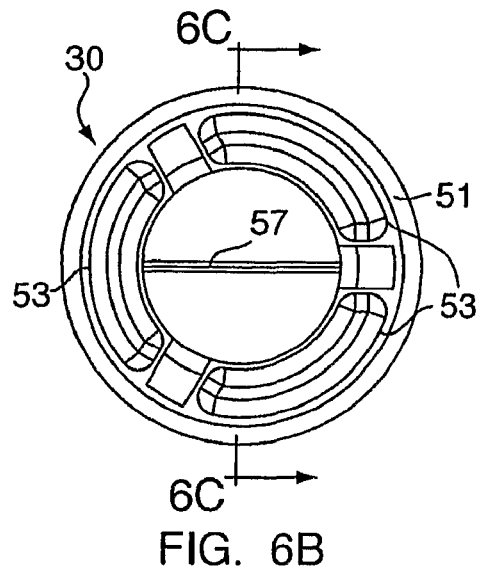
FIG. 6B is a bottom plan view of the self-sealing mechanism.
Figure 6C:
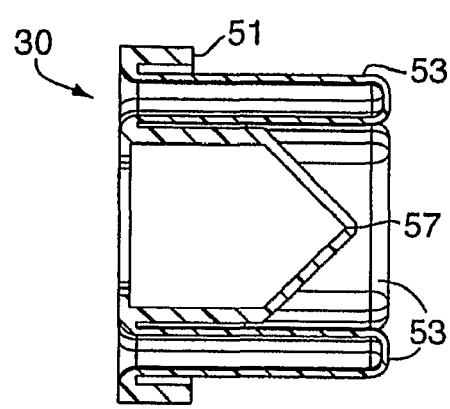
FIG. 6C is a cross-sectional view of the self-sealing mechanism taken along the lines 6C-6C of FIG. 6B.
Figure 6D:
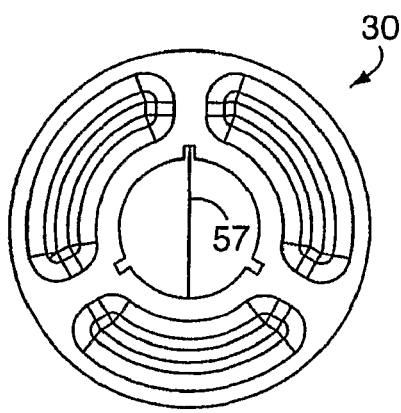
FIG. 6D is a top plan view of the self-sealing mechanism.
Figure 7A:
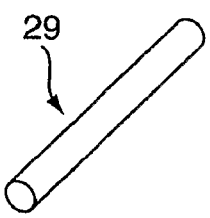
FIG. 7A is a perspective view of a trigger of a heat activating switch.
Figure 7B:
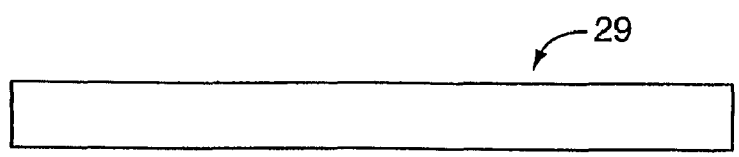
FIG. 7B is a side view of the trigger.
Figure 7C:
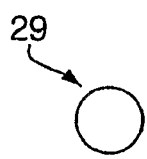
FIG. 7C is a plan view of the trigger.

With reference to FIGS. 1 through 3F, a white balance device embodying the present invention is indicated generally by the reference number 10. The device 10 comprises a housing or outer shell 12. The housing 12 has an outer surface 14 defining an opening 16 for inserting therein a medical videoscope such as a laparoscope or endoscope. An interior of the housing 12 defines a canal 18 having a first end 20 communicating with the opening 16 and a second end 22 terminating within the housing 12 for receiving a distal lens of a medical videoscope. A white balancing reference material 24 (see FIGS. 5A through 5C) is disposed within the housing 12 adjacent to the second end 22 of the canal 18.

The device 10 preferably accommodates a defogging material 26 adjacent to the second end 22 of the canal 18 for treating and preventing the distal lens of a medical videoscope from fogging during a medical procedure. The device 10 preferably further comprises a heating mechanism 28 in thermal communication with the canal 18 for heating an interior wall of the canal and the surgical defogging material 26 disposed within the canal to further prevent the distal lens of a medical videoscope from fogging. Alternatively, the heating mechanism 28 can be in thermal communication with the canal 18 for heating an interior wall of the canal to prevent a distal lens of a medical videoscope disposed in the canal from fogging when no defogging material is disposed in the canal. The device 10 further comprises a self-sealing mechanism 30 (see FIGS. 6A through 6D) disposed at least partly within the canal 18 and is configured for allowing a medical videoscope to enter the canal and make contact with the surgical defogging material 26 and for preventing the surgical defogging material from spilling out of the canal.

Preferably, the housing or shell 12 is made of an insulating foam material such as a medical grade polyurethane foam or any solid which can be a shock absorbing insulating material. The shell 12 can be designed to protect the lens of a medical videoscope or any other type of instrument from damage prior, during, and after a surgical procedure. The material is preferably inexpensive since the device 10 is preferably disposable and for single patient use. An outer cover of the shell 12 preferably is constructed of high density polyurethane, etha, viscoelastic, latex foams, and the like. The outer cover can also be made from rubber-like foam. A semi-flexible thermoplastic can also be used. The outer cover can also be made from insulating cardboard or a thick insulating fabric. The outer cover can alternatively be constructed out of a plastic frame covered by a silicone or insulating plastic. It is important that the material have good shock absorbing and insulating properties.

Figure 1:
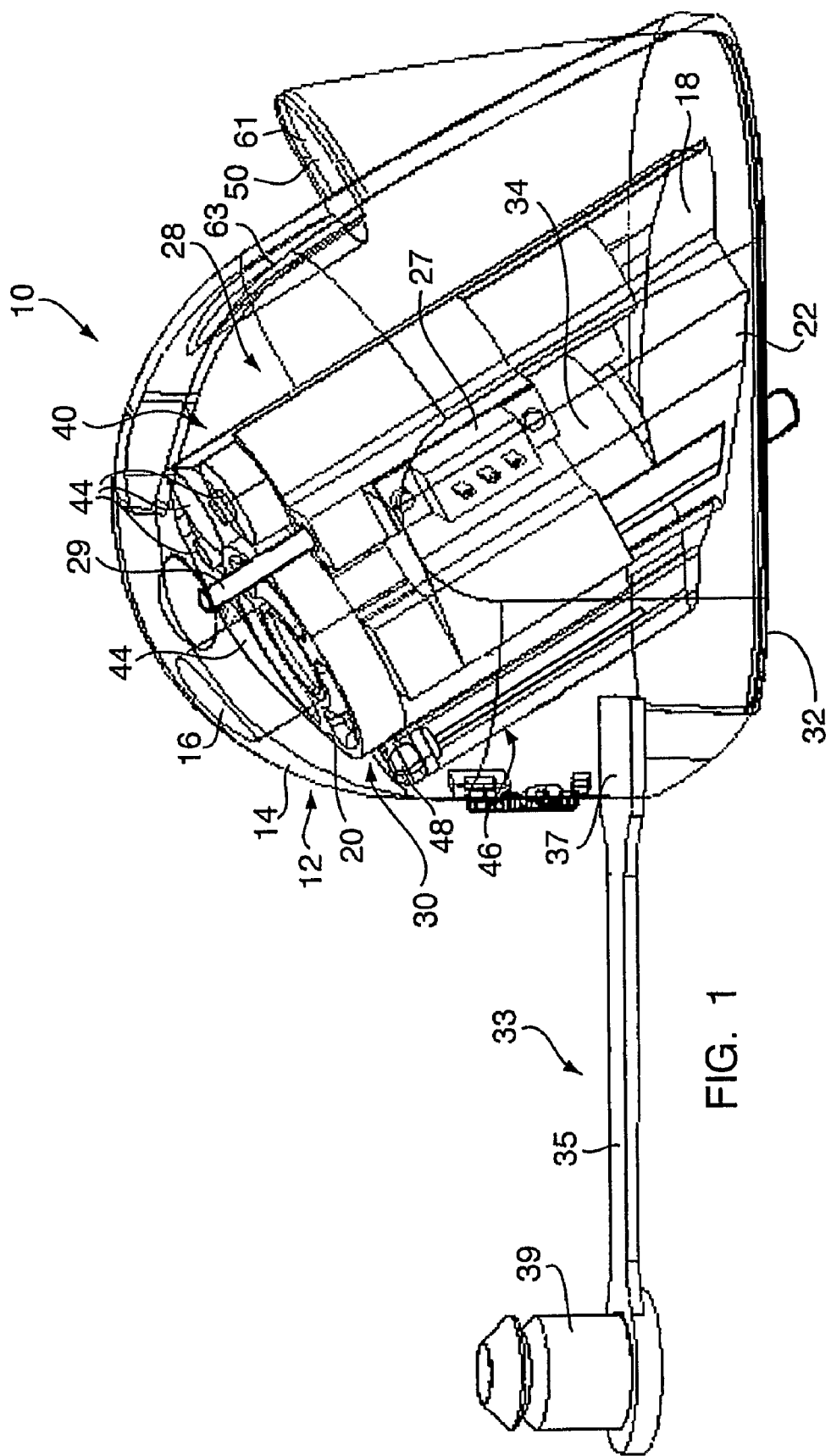
FIG. 1 is a perspective view of a white balance device embodying the present invention.

The device 10 is preferably shaped as in FIG. 1 but can alternatively be made in any other practical shape such as a cube, square or spherical shape. The device 10 can also have a tubular shape. The device 10 can have rounded corners or square corners. The device 10 exteriorly is preferably about 4 inches long, 3.5 inches wide, and 4 inches high, but generally can be as small as about 15 mm wide, 1 inch long, and 15 mm high. Alternatively the device 10 generally can be as large as about 6 inches wide, 6 inches long and 8 inches high. Clearly, the device 10 can be sized to accommodate the shape of any medical instrument used.

Figure 8A:
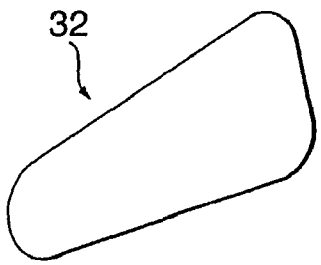
FIG. 8A is a perspective view of a securing mechanism.
Figure 8B:
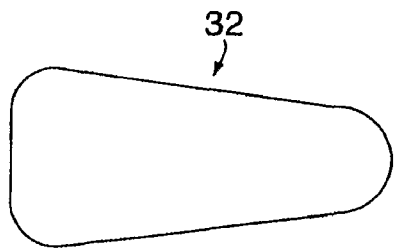
FIG. 8B is a plan view of the securing mechanism.
Figure 9A:
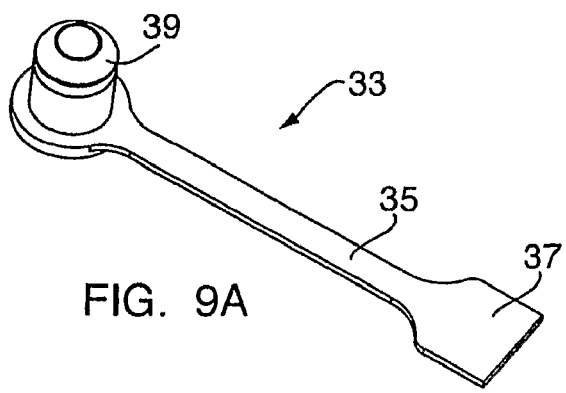
FIG. 9A is a perspective view of an insertion hole adapter.
Figure 9B:
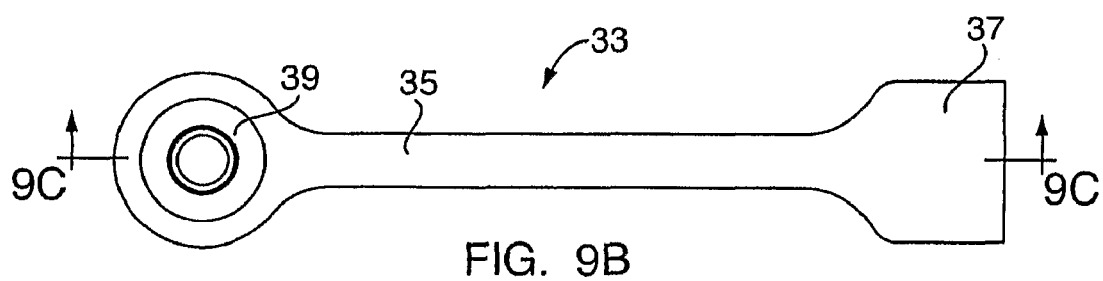
FIG. 9B is a plan view of the adapter.
Figure 9C:
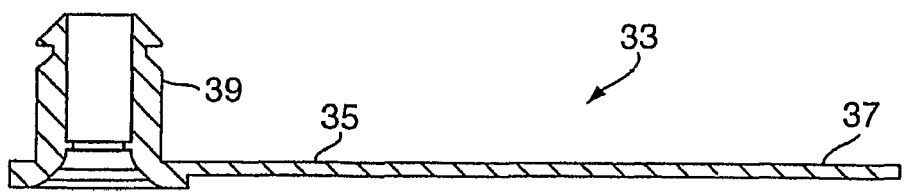
FIG. 9C is a cross-sectional view of the adapter taken along the lines 9C-9C of FIG. 9B.

The device 10 preferably includes a securing mechanism 32 (see FIGS. 2C, 8A and 8B) coupled to a bottom of the housing 12. For example, the securing mechanism 32 as illustrated is a solid flap, which can have the same perimeter as the base of the housing 12. This flap is attached only at the front bottom part of the device 10 so as to create a hinge. The flap is also preferably attached in the middle by two elastic bands. The flap can be constructed of a high-density foam material, cardboard or plastic. Preferably, the flap is constructed of a microfiber material. The external face of the bottom flap has an adhesive material that has a protective cover until it is needed.

When surgery begins and the surgeon brings the device 10 up to the operative field he can secure the device anywhere on top of the drapes by removing a protective cover from an adhesive bottom of the securing mechanism 32 and securing the device 10 anywhere on the operative field. The device 10 can also be secured by an assistant to a sterile equipment tray, from which a medical videoscope can then be passed to the surgeon. The function of the securing mechanism 32 as a flap is so that the scope can be inserted vertically, but when it is not in use the flap 32 allows the device 10 to rotate horizontally and rest on the drapes while the scope remains inside the device. Although the device 10 rotates along the hinge of the flap 32, the flap maintains the device 10 securely attached to the drapes with the adhesive coating.

Alternatively, the device 10 may be constructed without the flap 32 and adhesive can be placed directly on the bottom of the device. Furthermore, the device 10 can be secured to any surface through such components such as, but not limited to, adhesives, screws, magnetism, mounts, and clips. Moreover, the device 10 can remain unsecured to any surface and be put on and pulled off the scope as needed during the medical procedure.

As shown in FIGS. 1 and 9A through 9C, the device 10 preferably includes an opening adapter 33 to effectively reduce the diameter of the opening 16 for accommodating smaller diameter videoscopes. The adapter 33 includes a flexible longitudinal stem 35 having a base portion 37 at one end of the stem and a reduced opening portion 39 at another end of the stem. As shown in FIG. 1, the base portion 37 is coupled to a lower portion of the housing 12. The flexible longitudinal stem 35 is bendable in order to insert the reduced opening portion 39 into the opening 16 of the housing 12. The opening adapter 33 is preferably made of a flexible medical grade silicone plastic, but can also be constructed out of other flexible materials. The diameter of the reduced opening portion 39 is shown by way of example to be mm, but other sizes can be employed without departing from the scope of the present invention.

Figure 2A:
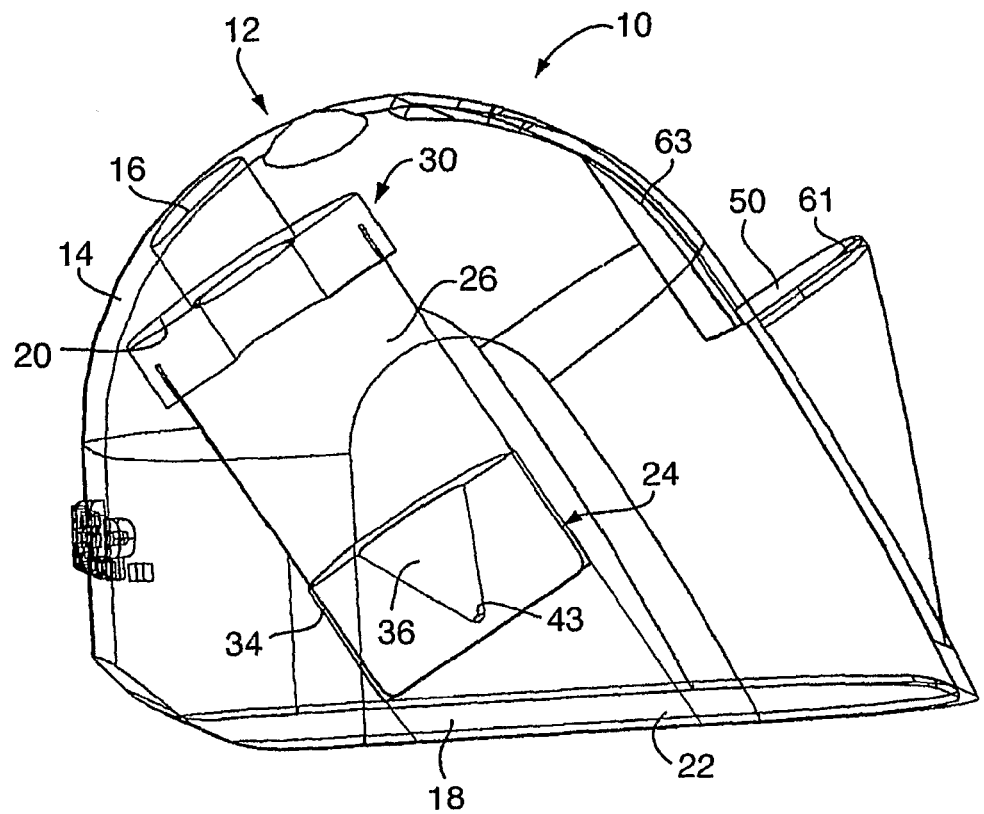
FIG. 2A is a side view of the device of FIG. 1 with heating components removed.
Figure 2B:
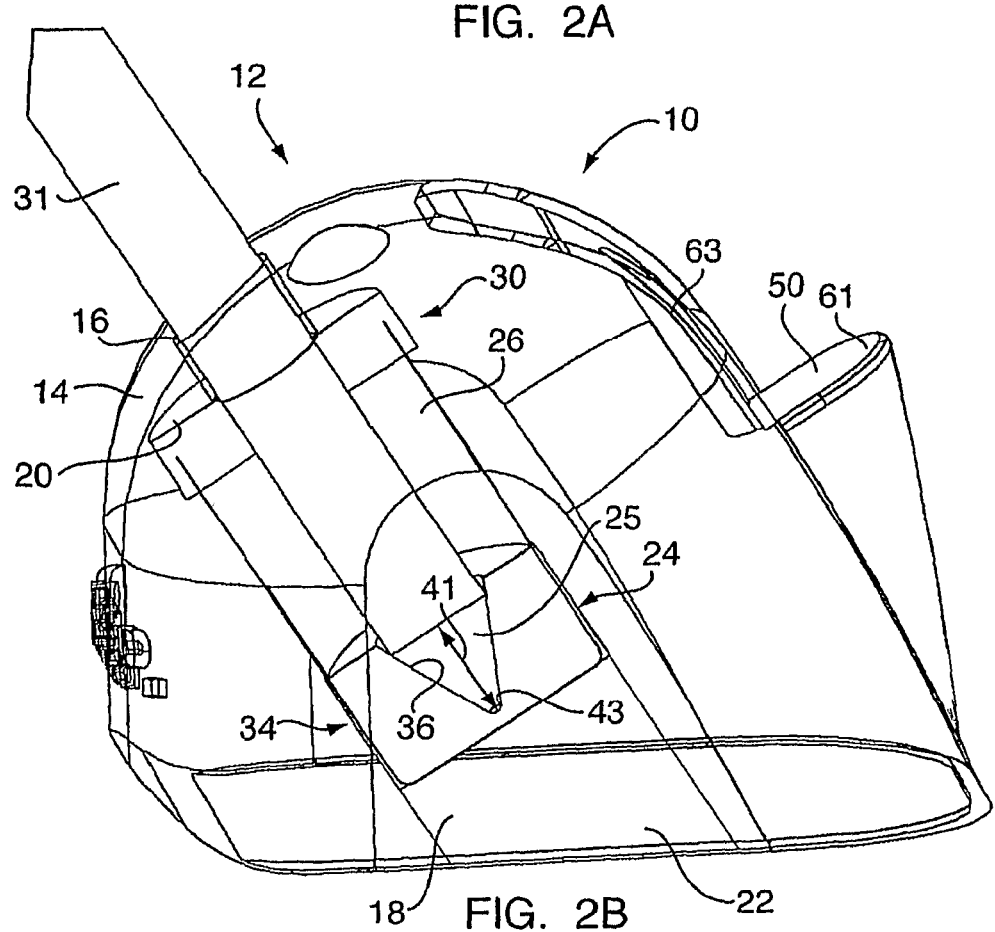
FIG. 2B is a side view of the device with a medical videoscope inserted therein.
Figure 2C:
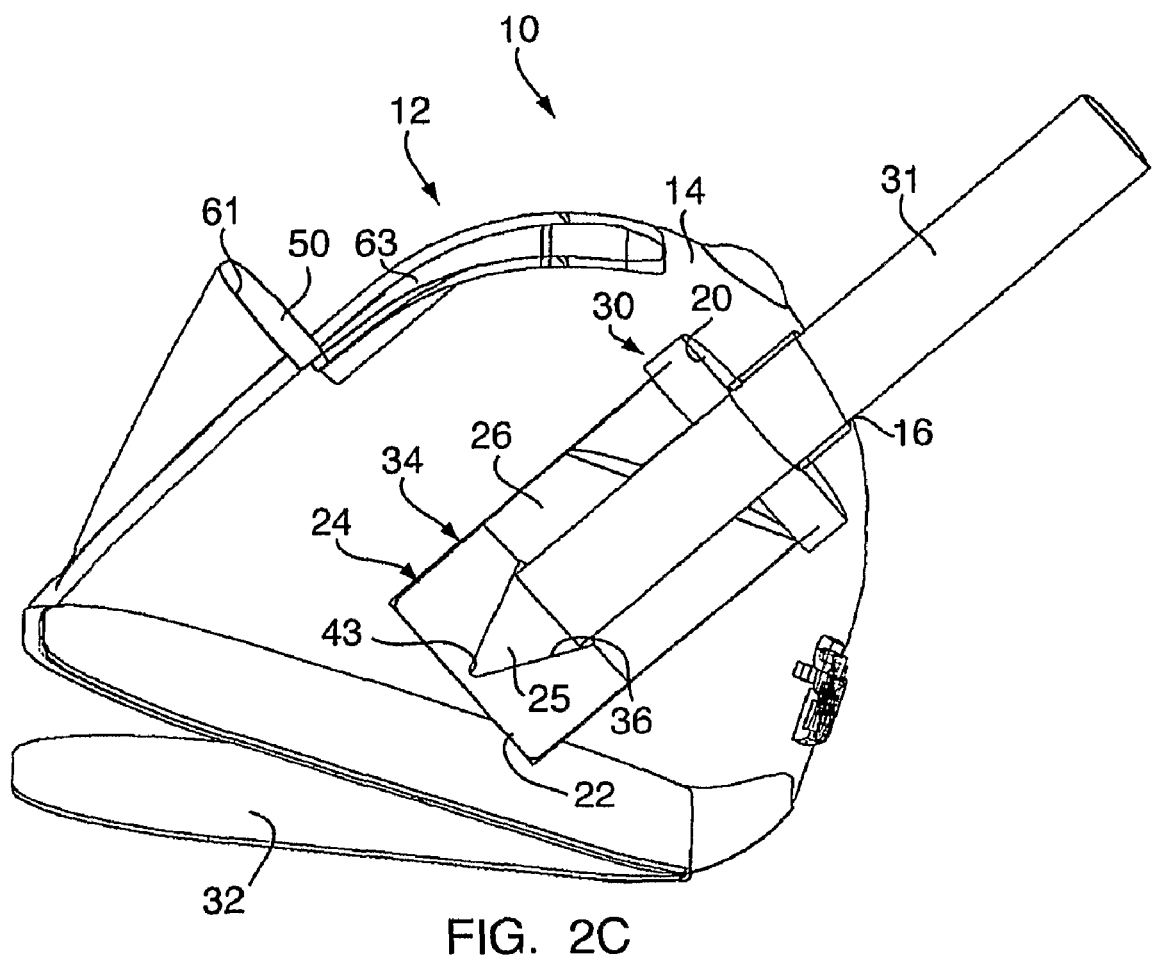
FIG. 2C is a perspective view of the device showing a securing mechanism.
Figure 4A:
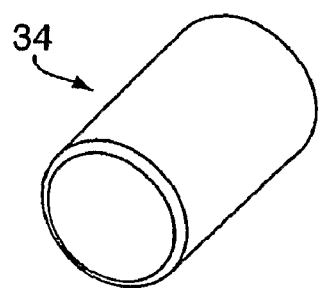
FIG. 4A is a perspective view of an embodiment of an inner chamber of a white balance device.
Figure 4B:
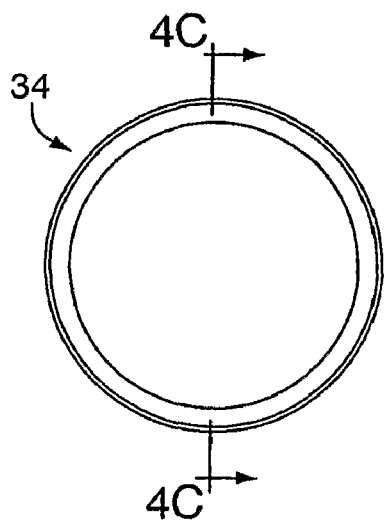
FIG. 4B is a plan view of the inner chamber.
Figure 4C:
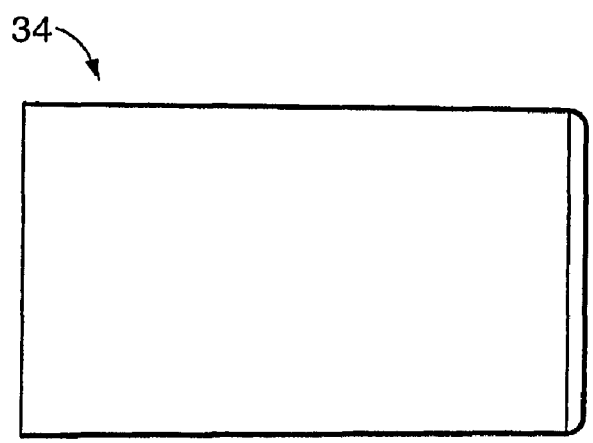
FIG. 4C is a cross-sectional view of the inner chamber taken along the lines 4C-4C of FIG. 4B.

FIGS. 2A through 2C show the white balance device 10 with the heating mechanism 28 removed for simplicity of illustration. The device 10 preferably includes an inner chamber or center sheath 34 (see also FIGS. 4A through 4C) defining the canal 18 and accommodated within a cavity of the housing. The canal 18 and the center sheath 34 are sized and shaped to accommodate a medical videoscope when inserted therein. The canal 18 and the sheath 34 preferably extend directly down the center of the device 10 from an upper front to a lower back portion. The sheath 34 can alternatively extend directly down a center or lateral to a center of the device 10. The location of the sheath 34 can be in any configuration as long as uniform thermal conductivity is achieved. The length of the sheath 34 is preferably about 3 inches long but can be as long as about 8 inches or as short as about 0.5 inches. The sheath 34 preferably has the shape of a tube. The tubular diameter inside the sheath can be about 5 mm, 10 mm, or any other practical diameter depending on the size and shape of the medical instrument to be inserted therein. The embodiment of the sheath 34 is preferably constructed of stainless steel or aluminum for good heat transfer properties, but may also be constructed of, but not limited to, a thin piece of high-density polyurethane, etha, viscoelastic or latex foam. The sheath 34 can also be made of rubber-like foam or thin plastic. A water impermeable fabric can also be used. The sheath 34 can alternatively be constructed of silicone or a rubber-like material. The sheath 34 can all be white or any other color.

As mentioned above, preferably the self-sealing mechanism 30 is disposed at least partly within the canal 18 and the sheath 34 to prevent the surgical defogging material 26 from spilling out of the opening 16 of the device 10. The canal 18 or the sheath 34 preferably accommodates the defogging material 26 such as an antifog, lens cleaning agent, or surfactant solution, and may lead into or define a reservoir which is filled with the defogging material.

An example of the self-sealing mechanism 30 is illustrated with reference to FIGS. 6A through 6D. The self-sealing mechanism 30 generally has the shape of a tube within a tube. Preferably, the self-sealing mechanism 30 is made of a flexible medical grade silicone plastic. The self-sealing mechanism 30 is configured to allow a medical videoscope to enter a reservoir at the second end 22 of the canal 18 or inner end of the sheath 34 and make contact with the defogging material 26 and prevent the defogging material when in the form of liquid or gel from spilling out of the opening 16 of the housing 12 when the device 10 is turned upside down while the scope is removed from the device. In other words, the self-sealing mechanism 30 is configured to function as a type of one-way valve to allow passage therethrough in only one direction.

As shown in FIGS. 6A through 6D, a preferred embodiment of the self-sealing mechanism 30 includes an upper lip 51 for being seated on the first end 20 of the sheath 34. The self-sealing mechanism 30 further includes three flaps or pockets 53 depending downwardly from the upper lip 51 and spaced from one another circumferentially about a periphery of the self-sealing mechanism 30 such that the pockets are facing an inner surface of the sheath 34. The self-sealing mechanism 30 has a center tube or duck bill 55 depending downwardly from the upper lip 51 and defines a slit 57 at a bottom portion thereof for permitting a scope to pass therethrough. The center tube 55 is spaced radially inwardly of the pockets 53 so as to define a space between the center tube and the pockets.

The self-sealing mechanism 30 prevents liquid from spilling out by creating and trapping liquid in the space around the first end 20 of the canal 18 or the sheath 34 defining the canal. When the sheath 34 is turned with the reservoir down all the liquid will fall into the reservoir. As the sheath 34 and the reservoir are turned upside down, the liquid slides along the side of the sheath 34 and enters the space of the self-sealing mechanism 30 surrounding the distal end of the sheath 34. The pockets 53 relieve pressure caused by a scope entering the reservoir. With a sealed enclosure provided by the center tube 55, as a scope is inserted through the center tube 55 pressure builds as the scope takes up space within the reservoir. The center tube or duck bill 55 is configured to prevent fluid or air from escaping, and thus the pressure build-up tries to force the scope out of the reservoir. The pockets 53 overcome such detrimental pressure build-up upon the scope. As the pressure builds, instead of pushing the scope out of the reservoir, the pockets deform taking up less space and balancing out the pressure. In other words, the pockets 53 are configured to serve as a pressure compensating system of the self-sealing mechanism 30.

Alternatively, the self-sealing mechanism can resemble a heart valve or be made with a flap and a hinge that only opens in one direction. The self-sealing mechanism can also resemble a valve in a human vein. Moreover, the self-sealing mechanism can be a ball and socket mechanism in which a ball inside the reservoir plugs the hole when the reservoir is turned upside down but still allows for the scope to enter in the other direction. The self-sealing mechanism is preferably constructed from a resilient plastic or other rubber-like material. It can also be made from a high-density foam or water impermeable fabric. The self-sealing mechanism can also be made of metal, aluminum, or silicone plastic. The self-sealing mechanism can be any configuration known to a person skilled in the art to prevent leakage and splash back of fluid.

As shown in FIGS. 2A through 2C, the white balancing reference material 24 is disposed adjacent to the second end 22 of the canal 18 such that when a lens 25 of a scope 31 is placed into the reservoir, the lens approaches within a predetermined distance of the reference material 24. The white balancing reference material 24 is preferably a true white, soft, non-scratch, absorbent material. The material must have a good light diffusing property. More preferably, the white balancing reference material 24 includes a sponge having a white color with a chromaticity of about D-65 or about a D-50 or about D-100. The white color of the white balancing reference material 24 is preferably equal parts of red, blue and green, but can have slight deviations designed to match the camera system specifications of the medical videoscope 31 to be white balanced by the reference material. The white balancing reference material 24 can be square in shape or in the shape of a rectangle. Alternatively the reference material 24 can be in the shape of an ellipse or a circle. The shape of the reference material 24 is dependent on the shape of the scope to be white balanced. The reference material 24 can be about ¼ to about 1/16 of an inch thick. The reference material 24 is made out of a low density foam or other soft material which can be either hydrophobic or hydrophylic. Preferably, the reference material 24 is made out of a white medical grade closed cell foam.

FIGS. 2B and 5A through 5C show the shape of the white balancing reference material 24 in a preferred embodiment. The reference material 24 preferably defines an indentation or narrowing portion 36 which is small enough for the distal lens 25 of the videoscope 31 to come into contact with the narrowing portion 36 and not to be able to further enter the reference material. The narrowing portion 36 is configured to maintain a predetermined space or distance 41 between the lens and a white surface of a facing base portion 43 of the reference material. The space 41 is of a sufficient distance to allow for proper white balancing of the videoscope 31.

The defogging material 26, preferably in the form of a gel or liquid, can be made of, but is not limited to, a combination of water, glycol, and a water-soluble wetting agent, alcohol, and a gelling agent. Preferably, when in the form of a liquid, the defogging material 26 is made from 1 part poloxamer 188, 99 parts water. A commercially available wound cleaning surfactant solution such as Shurclenz™ can be diluted with water and used. It may also use any other non-ionic surfactant alone or in a mixture. Alcohol may also be used in the solution. If a gelling agent is used, it can be a starch or any super absorbent polymer. Alternatively, a defogging solution can be used, and it can be any commercially available surgical defogging solution such as, for example, F.R.E.D.™ or E.L.V.I.S.™.

With reference to FIG. 1, the heating mechanism 28 is disposed adjacent to the reservoir of the second end 22 of the canal 18 or the sheath 34 so as to be in thermal communication therewith. The sheath 34 and the reservoir as part of the sheath are preferably made of stainless steel or aluminum for efficient heat transfer from the heating mechanism 28 to the defogging material 26 disposed within the reservoir. The heating mechanism 28 can include, for example, a heating element such as a wound 30 gauge copper wire or nichrome wire. The wire can be connected to a power source 40 such as a battery pack having a housing made of plastic (see FIG. 1) or to another source such as an AC outlet. When activated, electricity flows from the power source 40 through the heating element 38 so as to heat the reservoir and the defogging material 26 disposed therein.

A thermistor or switch 27 having a thermal component may be placed in the electrical circuit of the heating mechanism 28 to turn off the flow of electricity when a predetermined temperature is reached by the defogging material 26 so as to allow the heating mechanism to maintain a constant temperature of the defogging material above body temperature for an extended period of time while being energized by the power source 40 such as, for example, only four AAA batteries 44 electrically connected in series, as shown in FIG. 1. Although four AAA batteries 44 are shown by way of example, different size and different quantities of batteries may be used. Preferably, a trigger or plunger 29 (see FIGS. 1 and 7A through 7C) communicates with the switch 27. The plunger 29 is preferably made of stainless steel or aluminum, but may be also be formed of plastic or other generally rigid materials.

When the plunger 29 is pressed downwardly into the housing, the plunger initially doses the switch to electrically energize the heating mechanism 28 until the thermal component of the switch 27 opens the electrical circuit when the defogging material reaches the predetermined temperature.

The device 10 can also include an alert mechanism 46 so that upon activation a user is notified that the device is being heated by the heating mechanism 28. For example, the alert mechanism 46 can include a light such as an LED 48 (see FIG. 1) or an audible tone generator. Alternatively a thermometer or heat sensitive paint may be used as an indicator of activation.

The device 10 can also have a microfiber fabric 50 on all or part of the outer surface 14 of the housing 12 so that a scope lens can be wiped thereon and cleaned during a surgical procedure. The housing 12 preferably defines a ledge 61 and a depressed surface portion 63 which is covered by the microfiber 50 and against which a scope can be conveniently wiped clean. The microfiber 50 can be either permanently or removably attachable to the device 10. The microfiber 50 can be, but is not limited to, any combination of polyester and nylon.

As mentioned above, the sheath 34 and the reservoir may be constructed of stainless steel or aluminum, but any metal with good heat transfer properties can be used.

Because a medical videoscope is submerged in the defogging material in the form of a liquid or gel, the device 10 is a protector against fire hazards. This is because light from the scope is not allowed to be concentrated on any drapes or on the patient which could otherwise cause a burn or fire.

The device 10 may also be packaged in combination with other medical videoscopic care products such as microfiber surgical sponges, trocar wipes, and a microfiber patient cleaning set. The kit which contains this white balancing and defogging device of the present invention in combination with other medical videoscopic care products can be called a "laparoscopic care kit" or a "laparoscopic care pack".

Figure 10:
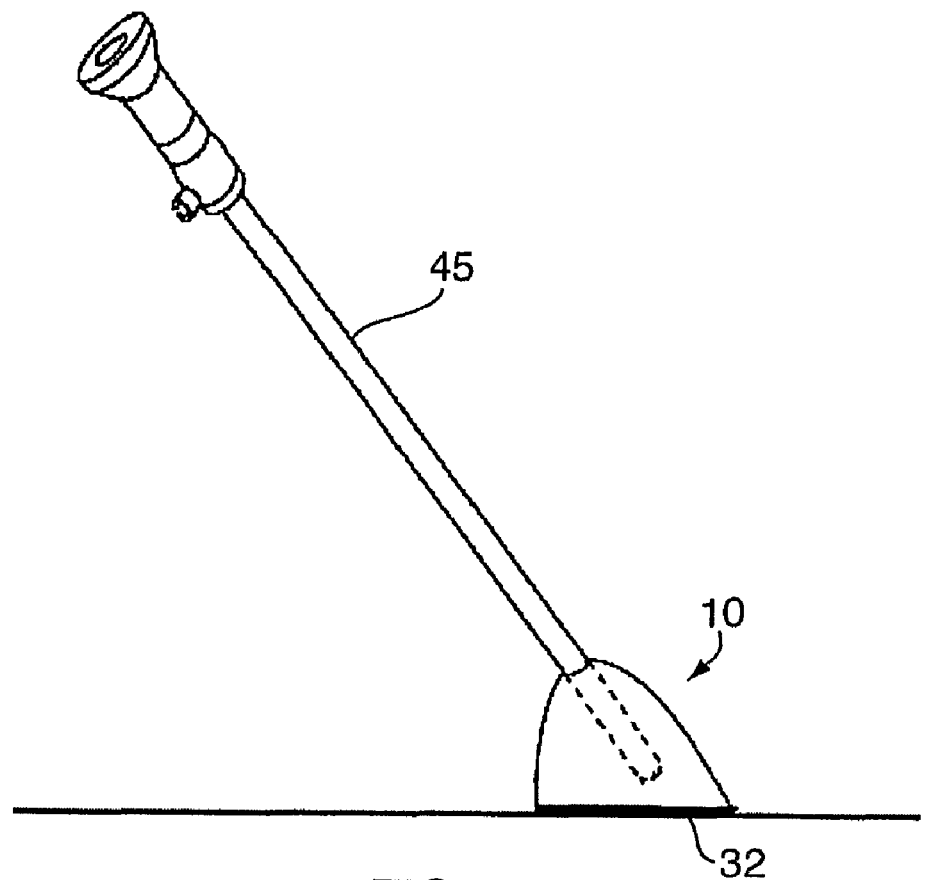
FIG. 10 is a perspective view showing a white balance device embodying the present invention oriented to maintain a laparoscope inserted therein in an upright position.

FIG. 10 is a perspective view showing a device 10 embodying the present invention oriented to maintain a videoscope such as, for example, laparoscope 45 inserted therein in an upright position.

Figure 11:
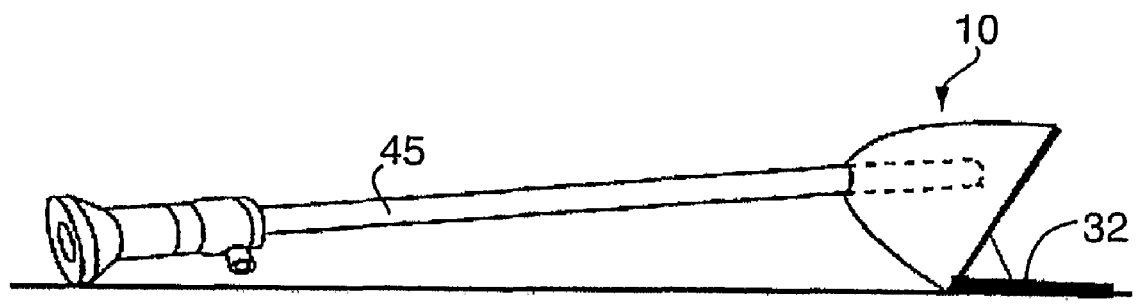
FIG. 11 is a perspective view showing the device of FIG. 10 oriented to maintain the laparoscope inserted therein in a resting position.

FIG. 11 is a perspective view of the device 10 of FIG. 10 oriented to maintain the laparoscope 45 inserted therein in a resting position. The securing mechanism 32 of the device 10 serves a hinge. There is an adhesive in the bottom of the device 10 that allows the device to be secured to drapes or to a table and still allow for the scope 45 to rest freely. This allows for the scope 45 to remain inside the device 10 so as to prevent a fire hazard whenever the scope is not in use.

While the above invention has been described with reference to certain preferred embodiments, the scope of the present invention is not limited to these embodiments. For example, although the white balancing reference material and defogging material are shown and described as being part of a single device, it should be understood that the white balancing reference material and defogging material can be disposed in separate devices working either simultaneously or non-simultaneously with one another without departing from the scope of the present invention. One skilled in the art may find other variations of these preferred embodiments which, nevertheless, fall within the scope and spirit of the present invention.

What is claimed is:

1. A device for white balancing a medical videoscope, comprising:

a housing having an outer surface defining an opening, an interior of the housing defining a canal having a first end communicating with the opening and a second end terminating within the housing for receiving a distal lens of a medical videoscope;

a white balancing reference material, the white balancing reference material being a sponge having a thickness disposed adjacent to the second end of the canal, the sponge having a generally conical recess formed therein for accommodating the distal end of the medical videoscope and having a base portion having a white surface facing the opening at the bottom of the conical recess;

a liquid or gel held within the sponge for defogging the distal lens of the medical videoscope; and a self-sealing mechanism including a one-way valve provided at the first end of the canal;

wherein the conical recess is defined by narrowing sidewalls such that when the distal lens of the medical videoscope is received in the conical recess the distal lens comes into contact with the narrowing sidewalls to limit an insertion depth of the distal lens in relation to the white surface.

2. A device as defined in claim 1, wherein the white balancing reference material has a white color with a chromaticity of generally equal parts of red, blue and green.

3. A device as defined in claim 1, wherein the white balancing reference material has a white color with a chromaticity of about D-50.

4. A device as defined in claim 1, wherein the white balancing reference material has a white color with a chromaticity of about D-65.

5. A device as defined in claim 1, wherein the white balancing reference material has a white color with a chromaticity of about D-100.

6. A device as defined in claim 1, wherein the surgical defogging material is disposed within the canal.

7. A device as defined in claim 6, further comprising a mechanism in thermal communication with the canal for heating the surgical defogging material.

8. A device as defined in claim 7, wherein the mechanism includes a heating element and a DC battery electrically coupled to the heating element.

9. A device as defined in claim 1, wherein the canal defined by the housing is configured for receiving a distal lens of an endoscope.

10. A device as defined in claim 1, wherein the canal defined by the housing is configured for receiving a distal lens of a laparoscope.

11. A device as defined in claim 1, wherein the housing includes a shock absorbing material.

12. A device as defined in claim 1, wherein the housing includes a thermally insulating material.

13. A device as defined in claim 1, wherein the self-sealing mechanism includes:

a tube or duck bill defining a slit configured for allowing a scope to enter through the slit and to prevent surgical defogging material from escaping through the slit; and at least one pocket disposed at least partly peripherally about the tube, the at least one pocket being configured for deforming to relieve pressure build-up between the tube and the at least one pocket as a scope enters the slit.

14. A device as defined in claim 13, wherein the at least one pocket includes three pockets spaced peripherally about the tube.

15. A device as defined in claim 1, wherein the self-sealing mechanism includes a tube within a tube.

16. A device as defined in claim 1 wherein the self-sealing mechanism is configured to resemble a heart valve.

17. A device as defined in claim 1, wherein the self-sealing mechanism includes a flap and hinge valve.

18. A device as defined in claim 1, wherein the self-sealing mechanism is configured to resemble a human vein.

19. A device as defined in claim 1, wherein the self-sealing mechanism includes a ball and socket valve mechanism.

20. A device as defined in claim 1, wherein the housing defines a reservoir adjacent to the second end of the canal for accommodating the surgical defogging material.

21. A device as defined in claim 20, wherein the white balancing reference material is disposed within the reservoir.

22. A device as defined in claim 1, further comprising a mechanism in thermal communication with the canal for heating an interior wall of the canal.

23. A device for white balancing a medical videoscope, comprising:

a housing having an outer surface defining an opening, an interior of the housing defining a canal having a first end communicating with the opening and a second end terminating within the housing for accommodating a surgical defogging material and for receiving a distal lens of a medical videoscope;

a white balancing reference material, the white balancing reference material being a sponge having a thickness disposed adjacent to the second end of the canal, the sponge including a generally conical recess for accommodating the distal lens therein and defined by narrowing sidewalls;

a liquid or gel held within the sponge for defogging the distal lens of the medical videoscope; and a self-sealing mechanism including a one-way valve disposed within the canal, the self-sealing mechanism being configured to allow for a medical videoscope to enter the canal and make contact with surgical defogging material and to prevent surgical defogging material from spilling out of the canal.

24. A device as defined in claim 23, wherein the self-sealing mechanism includes:

a tube or duck bill defining a slit configured for allowing a scope to enter through the slit and to prevent surgical defogging material from escaping through the slit; and at least one pocket disposed at least partly peripherally about the tube, the at least one pocket being configured for deforming to relieve pressure build-up between the tube and the at least one pocket as a scope enters the slit.

25. A device as defined in claim 24, wherein the at least one pocket includes three pockets spaced peripherally about the tube.

26. A device as defined in claim 23, wherein the self-sealing mechanism includes a tube within a tube.

27. A device as defined in claim 23, wherein the self-sealing mechanism is configured to resemble a heart valve.

28. A device as defined in claim 23, wherein the self-sealing mechanism includes a flap and hinge valve.

29. A device as defined in claim 23, wherein the self-sealing mechanism is configured to resemble a human vein.

30. A device as defined in claim 23, wherein the self-sealing mechanism includes a ball and socket valve mechanism.

* * * * *